United States Patent [19]
Neuss

[11] Patent Number: 5,536,274
[45] Date of Patent: Jul. 16, 1996

[54] SPIRAL IMPLANT FOR ORGAN PATHWAYS

[75] Inventor: Malte Neuss, Bonn, Germany

[73] Assignee: pfm Produkter für Die Medizin, Cologne, Germany

[21] Appl. No.: 98,303

[22] PCT Filed: Feb. 12, 1992

[86] PCT No.: PCT/EP92/00294

§ 371 Date: Oct. 1, 1991

§ 102(e) Date: Oct. 1, 1993

[87] PCT Pub. No.: WO92/14408

PCT Pub. Date: Sep. 3, 1992

[30] Foreign Application Priority Data

Feb. 15, 1991 [DE] Germany .................. 41 04 702.8

[51] Int. Cl.⁶ .................. A61F 2/06; A61F 2/04; A61M 29/02
[52] U.S. Cl. .................. 623/1; 623/12; 606/195; 606/194
[58] Field of Search .................. 600/36; 606/108, 606/194, 195, 198; 623/1, 12

[56] References Cited

U.S. PATENT DOCUMENTS

| | | | |
|---|---|---|---|
| 3,868,956 | 3/1975 | Alfidi et al. | 606/108 |
| 4,512,338 | 4/1985 | Balko et al. | 606/108 |
| 5,019,090 | 5/1991 | Pinchuk | 623/1 |
| 5,026,377 | 6/1991 | Burton et al. | 606/108 |
| 5,216,916 | 11/1993 | Engelson | 606/108 |
| 5,234,437 | 8/1993 | Sepetka | 606/108 |
| 5,256,146 | 10/1993 | Ensminger et al. | 606/198 |
| 5,306,294 | 4/1994 | Winston et al. | 606/108 |
| 5,312,415 | 5/1994 | Palmero | 606/108 |
| 5,354,295 | 10/1994 | Guglielmi et al. | 606/108 |
| 5,372,600 | 12/1994 | Beyar et al. | 606/108 |

*Primary Examiner*—Debra S. Brittingham
*Attorney, Agent, or Firm*—Keil & Weinkauf

[57] ABSTRACT

Spiral implant for organ pathways, in particular for blood vessels, which is formed from a primary spiral made of metal or a primary tube made of an elastic synthetic material whose anterior end is closed and whose cross-section at a distance of 0.5 to 2 mm from the other end of the primary spiral or primary tube is modified for a distance of 0.01 to 10 mm in order to make it possible to reposition the implant. The force required to displace the primary shape on the guide wire serving as an insertion aid amounts to 0.5N to 10N. The invention describes an implant (1) which can be used in vascular surgery or vascular radiology in order to achieve selective blood vessel occlusion. Insertion of the implant (1) into a blood vessel is brought about by means of an insertion catheter (16), with the implant being held in a rectilinear shape by a guide wire (14) slid therein. After the implant has reached the correct position in the organ pathway (18) it assumes a pre-formed spiral shape on the withdrawal of the insertion wire from inside it, thereby ensuring fixation of the implant in the organ pathway.

16 Claims, 4 Drawing Sheets

SPIRAL IMPLANT FOR ORGAN PATHWAYS

The invention relates to implants for organ pathways, preferably for blood vessels, whose secondary shape is formed either from a primary wire spiral made of metal or a primary tube made of synthetic material by twisting or winding, the secondary shape being extended for introduction and being reformed in association with placement in the organ.

In interventional radiology, metal spirals for vessel occlusion have, for more than 10 years, been implanted using catheters. Spirals of this type are described repeatedly in the literature. In Radiology 136;230–231 (July 1980), W. Castaneda-Zuniga et al. describe an improved form of the so-called Gianturco spirals, which can be introduced using catheters made of polyurethane or polyethylene. The primary spiral is formed by appropriate techniques into a ball or a secondary spiral. In order to be able to implant the spiral in its secondary shape, the latter is extended by drawing up the primary spiral onto a guide wire. When implanting by means of a catheter on the guide wire, a further displaceable spiral is arranged on the guide wire, which spiral serves to push the implant, i.e. the primary spiral, out of the catheter and to push it off from the guide wire, so that the secondary shape is reformed and the secondary spiral or the ball remains in the vessel which is to be occluded.

In Am. J. Roentgenol. 129:795–798 (November 1977) J. Anderson, S. Walace and C. Gianturco describe the advantages of being able to replace the spiral before finally casting it off. However, their helical corkscrew connection has the disadvantage that there is the danger of the vessel being perforated by the sharp end of the spiral. In addition, the spiral can be displaced by rotation while disconnecting. This is also suggested by the numerous complications in the animal experiments.

In Radiology 138;37–46 (January 1981), M. J. Mazer and coworkers describe the disadvantages of the known technique and refer to failures arising from incorrect choice of the size of the secondary spiral and to the risks of using unsuitable stripping devices.

A device for occluding arteries is described in DD-A-223 065, which device comprises a cardiac or angiographic catheter, with a prepared point, a pushing element (pusher), an occluding body and a core wire, on the front end of which wire the occluding body is slid on and is detachably secured. The core wire runs movably in the interior of the pushing element and can be introduced, together with the slid-on occluding body and the pushing element, beyond the opening of the catheter further into the artery in such a way that the occluding body remains on the core wire and is also conveyed by this wire outside of the catheter. By keeping a firm hold on the core wire and by further pushing of the pushing element, the occluding body can be stripped off the core wire. This can take place by retracting the core wire into the pushing element. The occluding body is provided with a textile fibre material over its whole length and over its whole periphery. It possesses a sleeve-shaped part at its posterior end into which the core wire can be introduced in such a way that the occluding body can be detached efficiently from the core wire using the pushing element.

An occluding body suitable for the intra-arterial and intravenous occlusion of blood vessels, is known from DD-A-158 084, in which occluding body a wire spiral is formed, with the use of relatively high degrees of deformation, into a helical spring body, such that the spring body, on the application of an external force, can be elastically reformed into a straight wire spiral and, on partial cessation of this force, assumes a knot-shaped configuration.

It is the object of the present invention to improve the constructional configuration of the implants in such a way that the possibility exists, before finally detaching the implants from the auxiliary means employed for the insertion, of, where appropriate, recovering these implants once again or else altering their position in the organ pathway.

This object is achieved by an implant for organ pathways which is formed from a primary spiral made of metal or a primary tube made of elastic synthetic material, in which the anterior end of the primary spiral or of the primary tube is closed and the posterior region is formed as a clamping seat for a guide wire, characterized in that, at a distance of 0.5 mm to 2 mm from the posterior end of the primary spiral or of the primary tube, its cross-section is modified for a distance of 0.01 mm to 10 mm by diminution of the internal diameter in at least one radial direction, so that the force required to displace the primary spiral or the primary tube and to overcome the clamping force with the guide wire serving as an insertion aid is 0.5N to 10N, the implant has a secondary shape of increased external diameter, which shape can be extended by the primary spiral or the primary tube being slid onto the guide wire and reforms on pulling out the guide wire or on pushing off from the guide wire as a result of restitutory forces present in the material. Forces between 1.5N and 3N are preferred.

The primary spirals having diameters of 0.2 mm to 3 mm, preferably 0.4 mm to 1.5 mm, are wound from metal wire having diameters of 0.06 mm to 0.6 mm, preferably 0.1 mm to 0.4 mm, and the secondary shape is formed subsequently. However, the shape can also be formed at the same time as the primary spiral is being wound. Suitable materials for the implants having a primary spiral made of metal are surgical steel wire with spring properties, corrosive or non-corrosive spring steel wire and steel wire made of non-precious metals, which is coated with corrosion-resistant metals such as tantalum, titanium, platinum or gold, or ceramic materials. The wire can have a round, oval or rectangular cross-section.

The primary tubes for implants are prepared from medically compatible elastic thermoplastic polymers, such as polyurethane homopolymers or copolymers, polyolefin copolymers or silicone elastomers. Resorbable polymers, such as aliphatic polyesters, e.g. polydioxanone, are also suitable, and the secondary spiral shape is formed subsequently. The wall thickness of the primary tubes can be 0.08 mm to 0.8 mm, and the diameter of the primary tubes 0.3 mm to 3 mm. The constriction of the cross-section for achieving a clamping seat, in the case of primary tubes, can also take place by parallel elongated slots being cut in over the circumference of the tube, and longitudinal strips of the polymer material being permanently deformed inwards by being pressed in. The advantage of this configuration of the cross-sectional constriction for producing a clamping seat on the guide wire is that the longitudinally extending sections which have been formed exhibit an enlarged contact surface on the guide wire.

The length of the primary shapes, i.e. of the primary spirals or primary tubes, can be 10 to 500 mm, preferably 10 mm to 200 mm.

It is a characteristic of the implants according to the invention that the secondary spiral shape can be reversibly extended by sliding the primary spiral or the primary tube onto a guide wire, whose diameter is somewhat smaller than the internal diameter of the primary spiral or the primary tube in the non-modified parts, and that the secondary shape is reformed on pulling out the guide wire or on pushing off from the guide wire as a result of restitutory forces present in the material. An elastic spring behaviour of this nature, and the restitutory forces resulting from it, are based on the properties of the selected materials. The spring action can, for example, be achieved by heating the material, which has been configured into the desired shape, and subsequently cooling (quenching) it rapidly. The spring action of thermoplastic polymers frequently depends on the formation of particular crystalline structures, or on the freezing in of stresses in the material during shaping. The measures for establishing the modulus of elasticity of the material necessary for the reversible extension, and the selection of the materials which are suitable for this, are known to the person skilled in the art and do not present him with any difficulties.

By means of the part formed with a modified cross-section in the vicinity of the rear end of the primary shape of the implants, a clamping seat is achieved of the primary shape, that is approximately the extended secondary shape on the guide wire, in association with which, however, the clamping force is not so great that displacement of the primary shape on the guide wire and complete withdrawal of the guide wire, or stripping from the guide wire by means of a stripping element, is no longer possible.

The placement of the implant is effected using a device having an insertion catheter, a stripping element and a guide wire for the implant, the guide wire being provided with a conical point and possessing, immediately after the point, either an annular groove or a circumferential beading, in order to achieve a particularly high clamping effect between the posterior region of the implant, with reduced internal diameter, and the anterior region of the guide wire.

For insertion into an organ pathway, the guide wire, with the stripping element slid onto it and the primary shape of the extended implant slid on in front of the element, is placed inside a catheter. With a solid cross section, the diameter of the guide wires can be 0.07 to 0.7 mm. The ability to reposition the implant is given by the static friction of the part with the modified, preferably reduced, cross-section on the guide wire being 2 to 5 times, preferably 2 to 3 times, greater than the force which is necessary in order to stretch once again the secondary shape, which to a large extent has been completely formed in the organ pathway as the result of partial stripping from the guide wire, by retracting it into the insertion catheter. The selected upper limit of the clamping force ensures that, in the event of unwanted catching of the implant in the wall of the organ pathway, damage to the latter by too great a withdrawal force is avoided. The clamping seat of the primary shape of the implant on the guide wire is achieved by the cross-section of at least one to several turns of the primary spiral being modified by constriction of the diameter of the primary spiral., or by formation of an oval cross-section whose smaller diameter is smaller than the external diameter of the guide wire. The desired difference between withdrawal force into the insertion catheter and the force for overcoming the clamping seat of the primary shape on the guide wire can, with the given modified cross-section of the primary shape, also be brought about by using a guide wire with a friction-increasing surface configuration, for example a roughened surface, in the anterior region, with a circumferential beading, or by means of an annular groove in the guide wire in which the modified, preferably constricted, cross-section at least partially engages.

The device described above permits reliable placement of the implant according to the invention in an organ pathway, going through the following steps:

a) advancement of the catheter, in whose inner lumen the implant is located in extended condition on the insertion wire, inside the organ pathway into the vicinity of the site where the implant is to be located, b) displacement of the insertion wire, with the implant located on it in extended shape, to the intended site for the location, c) formation of the secondary shape of the implant by withdrawing the guide wire or by pushing forward the stripping element, d) further withdrawal of the catheter and of the guide wire, or pushing forward of the stripping element, until only the anterior point of the guide wire is held in the clamping seat in the posterior region of the primary spiral or the primary tube, e) correction of the position of the implant, or, if necessary, withdrawal of the implant into the catheter, f) stripping-off of the implant from the guide wire at the site intended for it in the organ pathway using the stripping element.

The secondary shapes of the implants according to the invention can exhibit varying forms, in each case according to the special intended effect in the organ pathway.

As a prosthesis for an organ pathway, a cylindrical form is preferred in which the external diameter of the cylinder must be at least as large as the internal diameter of the organ pathway to be supported, in order to guarantee secure placement. In order to reduce the risk of thrombosis, it is preferred, in this mode of application, to heparinise the surface of the implant. In the case of implants made of polymers, the chemical bonding of heparin to the polymer presents no problems, and is known to the person skilled in the art. In the case of implants made of metal, the binding of the heparin can necessitate the application of a thin adhesive layer of a medically compatible polymer which is capable of chemical bonding. Since the suitable polymers, such as, for example, polyvinyl alcohol, silicones, or copolymers with heparin-binding groups based on polyurethanes or polyolefins, possess film-forming properties, the polymers can be applied either from a dispersion, emulsion or solution in organic solvents, and the film can be formed by evaporating off the liquid medium.

In order to configure the open inner cross-section of prostheses of this type to be as large as possible, the primary spiral or the primary tube of the implant can have an oval cross-section, and the cylindrical secondary shape can be so formed that the surfaces with the larger radius of curvature of the primary shapes are arranged alongside each other in the secondary shape, and form the outer surface of the secondary shape.

However, a contrary effect of the implants is frequently desired; organ pathways are to be constricted or occluded by the implant. In order to achieve this with a cylindrical secondary shape, either the diameter can be formed to be correspondingly small, or a cylindrical spiral can be wound in which turns of varying diameter alternate so that the internal diameter of the secondary shape is variably formed in the lengthwise axis of the spiral, with individual turns or several turns of the minimum possible radius of curvature. A constriction of an organ pathway can also be achieved by means of a cone or a double cone with the larger diameter at the ends of the secondary shape. In this way, flows in vessels (via catheters) can be throttled. In this context, the minimum internal diameter should not be less than 4 mm, if the vessel must remain open. (One possible application is pulmonary banding in children with left-right shunt).

For an occlusion, a shape which is here designated a helix is particularly suitable. In this case, the primary shape is wound helically, with the primary shape being bent off in the centre at right angles to the helix and, at a distance from the first helix, a second helix being formed parallel to it, which second helix can, where necessary, also have a smaller or larger diameter. The primary shape between the two helical elements can also be wound as a spiral, in order to provide the secondary shape with greater stability in the direction of the lengthwise axis. When being used for occlusion in association with a cardiac septum defect, this secondary shape can yield elastically to the alterations in wall thickness at each heartbeat.

In order to increase the rigidity of the external turns of the helix or of the double-cone shape, the wire used to prepare the primary spiral or primary shape can also, instead of a relatively large round cross-section, have an oval or rectangular cross-section.

Since, particularly in perinatal use, the external diameter of the insertion catheter should be as small as possible, and consequently the spiral diameter of the secondary shape must necessarily also remain small, this can lead, in the case of larger organ pathways to be occluded, to problems of stability in association with arrangement and location, with the danger of incomplete occlusion or of dislocation. In such a case, it is particularly preferred to locate double cones as implants in the organ pathway in a tandem arrangement. For carrying out the location, two secondary shapes, in each case formed as a double cone, are arranged behind one another in extended form on the guide wire. The first double cone with a permanent inner lumen is implanted, and subsequently the second implant, in extended form, is pushed so far forward that the anterior end projects beyond the first double cone to be implanted, and partially unrolls. By further withdrawal of the guide wire, while the stripping element is stationary, a central part of the double cone is deposited in the inside of the first double cone in more or less extended form, and the end of the second double cone outside the first double cone unrolls. The elastic force of the second implant, which is still extended in the inner lumen of the first double cone, pulls the first implant as tightly together as possible and enlarges the external diameter of the ends of the double cone, and increases the contact pressure on the organ wall. At the same time, the inner lumen is additionally closed. The minimum external diameter in association with catheter occlusion is only 1.3 to 2.3 mm (4° F. to 7° F.) in this technique, so that this implantation technique can also be employed with neonates or premature babies. If the smallest implant is supplied in a normal cannula, the smallest external diameter then amounts to only 1 mm, and thus permits use in a relatively risk-free manner even at the prenatal stage, e.g. for aneurismal occlusion.

Since a thrombotic effect is desired in association with the occlusion of an organ pathway, the surface of these implants is not heparinised but, on the contrary, is given a coagulation-promoting configuration. This can take place by coating the surface with metal particles, silicones, polytetrafluoroethylenes, medically compatible rubber latices, or with medically compatible polymers which promote blood coagulation.

For plugging cavities and vessels, a secondary shape of the implant is in particular suitable which possesses several loops lying behind each other in the form of horizontal figures of eight.

The invention is described below in still more detail with reference to the illustration.

BRIEF DESCRIPTION OF THE DRAWINGS

FIGS. 7, 7a and 7b show the implant shape of the so-called double helix and double rosette from the side and from behind.

FIG. 8 shows diagrammatically a preferred embodiment of the anterior end of an insertion wire for implanting the spirals according to the invention.

FIG. 9 shows the anterior end of an insertion catheter in longitudinal section.

FIG. 10 shows in cross-section the end of an insertion catheter which was represented in FIG. 9.

FIG. 11 shows diagrammatically, in sequence a to e, the individual steps involved in locating an implant according to the invention in an organ pathway.

Figure 1:
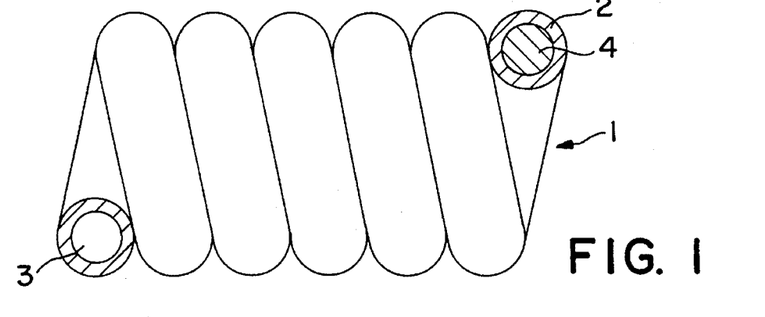
FIG. 1 shows diagrammatically a cylindrical secondary shape of the implant which, with a small spiral diameter, can be used to occlude a narrow organ pathway or, with a larger diameter, can be used as a prosthesis for keeping an organ pathway open.

The implant shown in FIG. 1 has the secondary shape 1 of a cylindrical helix or spiral, the helix 1 itself being composed of a wire spiral 2 (primary shape) made of spring metal. The modification of the cross-section 3 of the primary spiral 2 at the posterior end is not shown in this figure. The anterior end 4 of the primary spiral 2 is closed in order to ensure that, on extending the secondary shape on the insertion wire, the primary spiral 2 cannot be drawn so far up the insertion wire that the latter projects beyond the end of the primary spiral 2.

Figure 2:
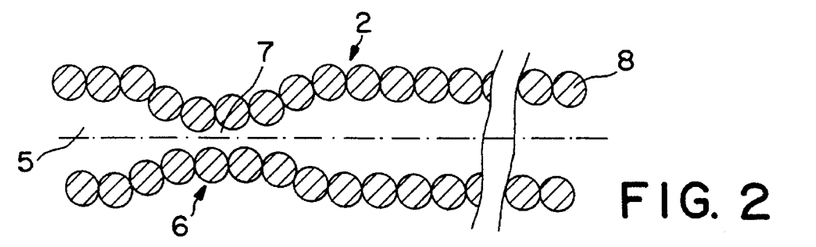
FIG. 2 shows diagrammatically in longitudinal section a part of the posterior end of the primary shape of the implant spiral from FIG. 1.

In FIG. 2, the posterior end of the primary shape of the implant from FIG. 1 is reproduced in enlarged form. The internal diameter of the primary spiral 2, which is wound out of metal wire having spring properties, is constricted at a short distance from the posterior end 5 by means of turns 6 which have a smaller diameter. If the primary spiral 2 is slid onto an insertion wire whose external diameter is somewhat larger than the modified internal diameter 7 of the primary spiral 2, the clamping seat of the extended secondary shape on the insertion catheter, which seat is desired for the repositionability, is formed.

Figure 3:
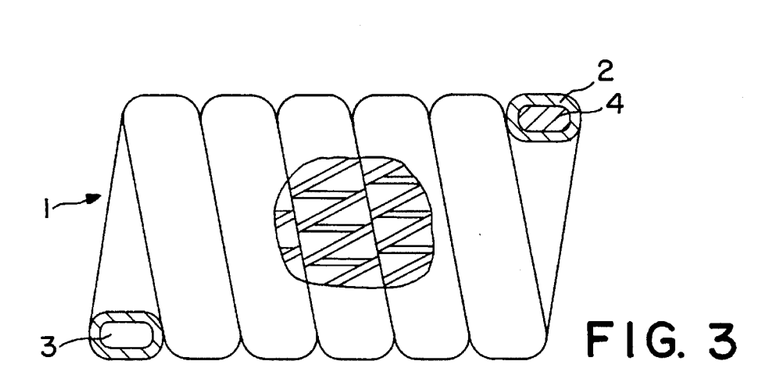
FIG. 3 shows diagrammatically a cylindrical secondary shape of the implant spiral whose primary shape differs from the primary shape in FIG. 1 in its cross-sectional shape.

The cylindrical spiral 1 represented in FIG. 3 is formed from a primary shape 2 whose cross-section 3 is oval. The anterior end 4 of the primary spiral 2 is closed. This shape is particularly suitable as a prosthesis for organ pathways because, as compared with the shape shown in FIG. 1, a somewhat larger free internal volume of the prosthesis remains.

Figure 4:
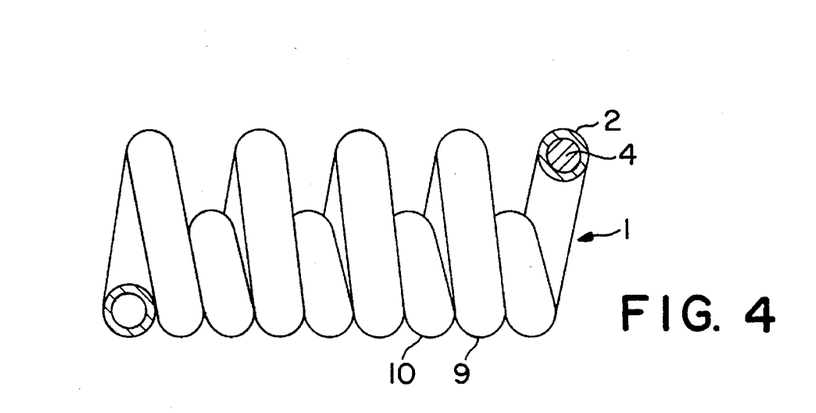
FIG. 4 shows diagrammatically a cylindrical secondary shape of the implant with spiral twists of varying diameter.

FIG. 4 shows a cylindrical shape of the secondary shape 1, which was formed from a primary spiral 2. The anterior end 4 of the primary spiral 2 is closed. In order to form the implant to be particularly suitable for occluding organ pathways, the secondary shape 1 possesses turns 9, 10, of different diameter, which alternate with each other. The turns of the implant having the larger diameter 9 serve to support the implant against the wall of the organ pathway and the turns 10 having the smaller diameter reduce the free internal volume of the implant and thereby promote occlusion through thrombosis.

Figure 5:
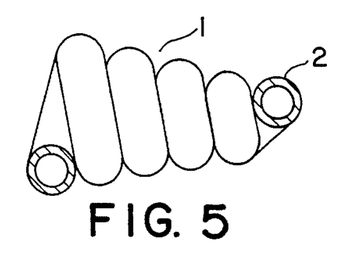
FIG. 5 shows diagrammatically a conical shape of the implant.

FIG. 5 shows the configuration of a conical secondary shape 1 from a primary spiral 2. In order to simplify the positioning, and retraction into the insertion catheter, of a spiral which has been partially paid out but which has still not been completely stripped from the guide wire, the cross-sectional modification, in the conical configuration, is preferably arranged at a distance from the end of the secondary spiral 1 which has the smaller diameter. However, the modification of the cross-section can also be arranged at the end of the spiral having the larger diameter.

Figure 6:
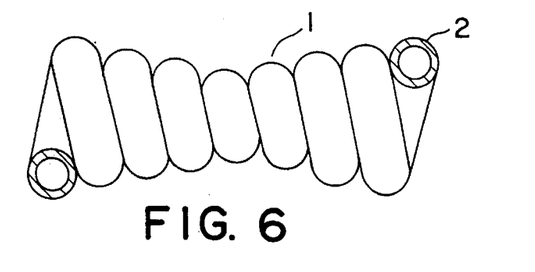
FIG. 6 shows diagrammatically an implant in the form of a double cone.

FIG. 6 is a particularly preferred embodiment of the helical implant according to the invention in the form of a double cone, the turns of the secondary shape 1 being arranged with a smaller diameter in the central region, and the ends possessing a larger turn diameter. In the figure, the external diameter of the secondary shape 1 is identical at both ends. In principle, however, it is also possible to form the double cone in such a way that the secondary shape has a different diameter at each of the two ends.

Figure 7:
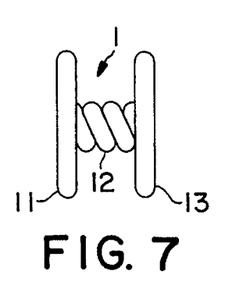
FIG. 7 demonstrates the implant as a double helix.

FIG. 7 shows the shape of the implant according to the invention which is designated here as a double helix. The secondary shape 1 is composed of two parallel elements 11 and 13 which are spaced apart from each other, wound helically and connected to each other by means of a cylindrically wound intermediate piece 12, which runs in the direction of the lengthwise axis of the double pieces, the elements 11 and 13 extending at right angles to the lengthwise axis. In principle, however, it is also possible for the double helix to be formed in such a way that it has different diameters at each of the two ends.

Figure 7A:
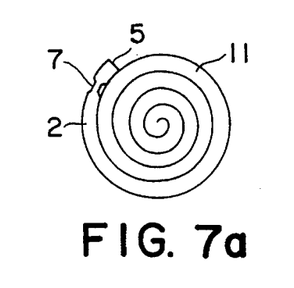
FIG. 7a demonstrates the implant helically rolled up with a constriction a short distance from the posterior end.

FIG. 7a shows one of the helically rolled-up elements 11 with a diagrammatically indicated primary shape whose diameter is modified, i.e. formed to be constricted, in the section 7 at a short distance from the posterior end 5.

Figure 7B:
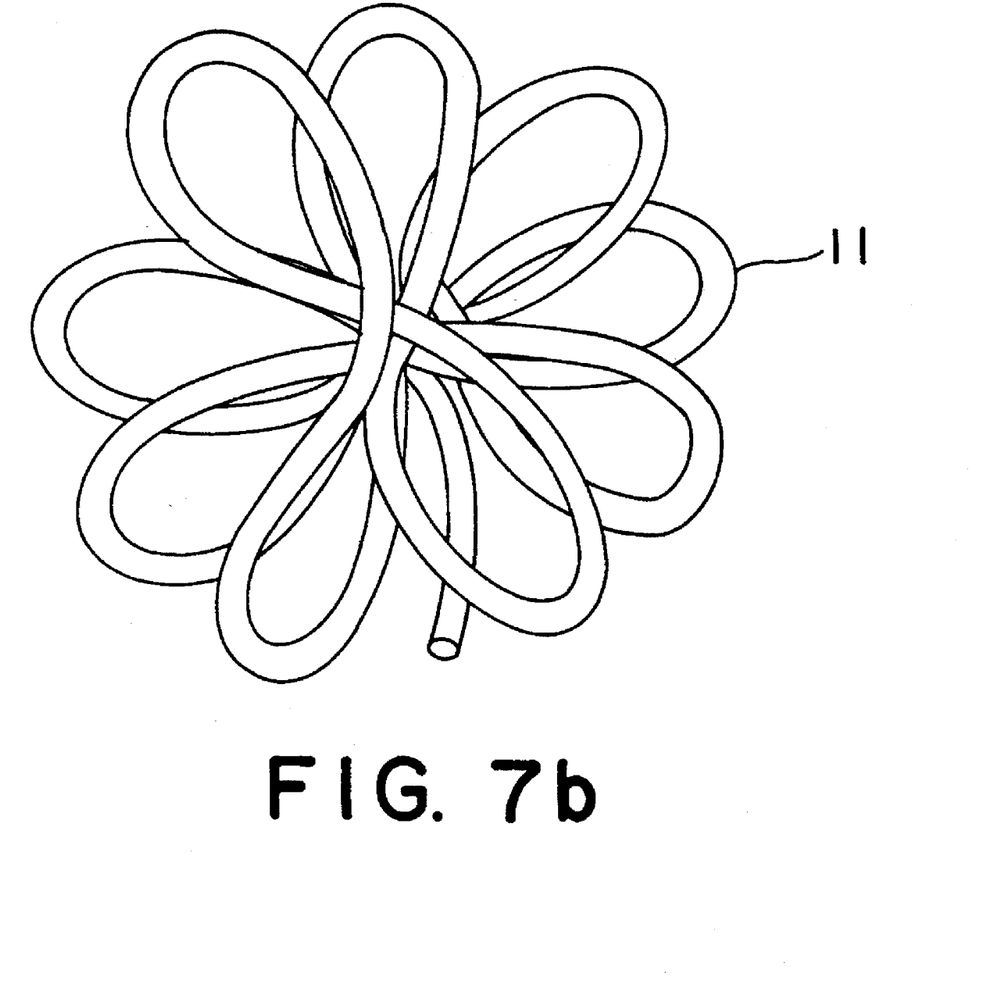
FIG. 7b demonstrates the implant configured as a rosette.

It is evident from FIG. 7b that the helically rolled-up elements 11 can also be configured as a rosette in order to form a double rosette instead of a double helix.

Naturally, all the secondary shapes which are preferred according to the invention and which are formed from spirals (primary shape) can also be formed from elastic tubes made of synthetic material.

Figure 8:
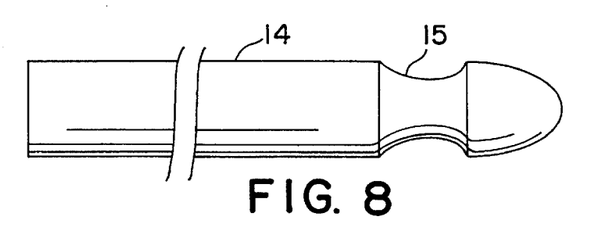
FIG. 8 demonstrates a guide wire used to support the clamping seat of the implants.

In order to support the clamping seat of the implants according to the invention on the insertion wire in a particular position shortly before the final release, a guide wire can be used whose anterior end is represented diagrammatically in FIG. 8. In order to simplify the sliding-on of the primary shape of the implant onto the insertion wire 14, the anterior end of the latter is preferably rounded off conically, and an annular groove 15 is formed at a distance from the anterior point, into which groove the section with the modified cross-section of the primary shape of the implant according to the invention engages, so that the clamping seat is particularly pronounced at this point, and the maximum force for overcoming the clamping seat while stripping off the implant from the guide wire is determined by the force for releasing the engagement of the modified turns of the primary spiral or of the modified cross-section of a primary tube with the annular groove 15.

Figure 9:
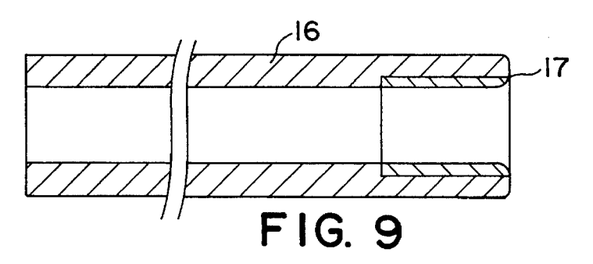
FIG. 9 demonstrates, in longitudinal section, the anterior end of a catheter which is suitable for insertion of the implants.

FIG. 9 shows, in longitudinal section, the anterior end of a catheter 16 which is suitable for inserting the implants according to the invention into organ pathways, into the tip of which catheter preferably a liner 17 made of metal or of a hard, particularly low-friction, polymer material is firmly inserted. In order to simplify the retraction, for the purpose of repositioning, of secondary spirals which have already been partially formed into the catheter, the front end of the lines directed toward the exterior is rounded off inwards. This strengthening liner extends that part of the implant which has already been pushed off the guide wire to such an extent that, after pulling into the catheter, it can be removed once again from the organ pathway together with the catheter in order to make possible a repositioning during a new insertion cycle. This can prove to be necessary in particular when it emerges, in association with the partial formation of the secondary shape in the organ pathway, that an unsuitable implant shape has been selected, or else that the formation of the secondary shape has not taken place in the correct position in the organ pathway.

Figure 10A:
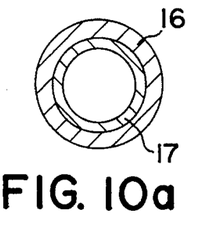
FIGS. 10a–c demonstrate strengthened catheter tips in cross-section.
Figure 10B:
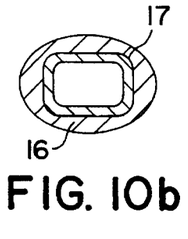
Figure 10C:
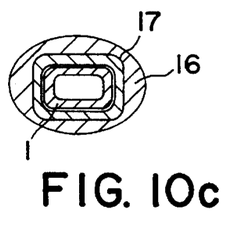
Figure 11A:
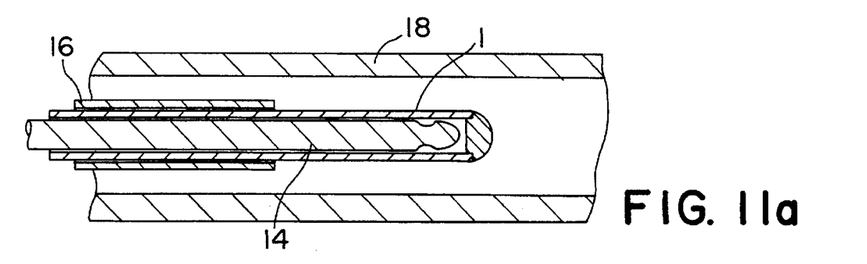
FIGS. 11a–e demonstrate the positioning of the implant in an organ pathway.
Figure 11B:
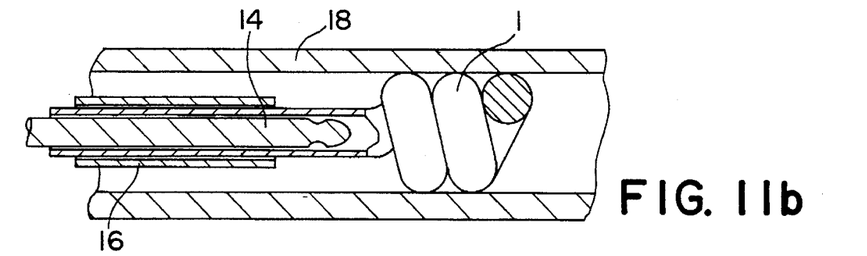
Figure 11C:
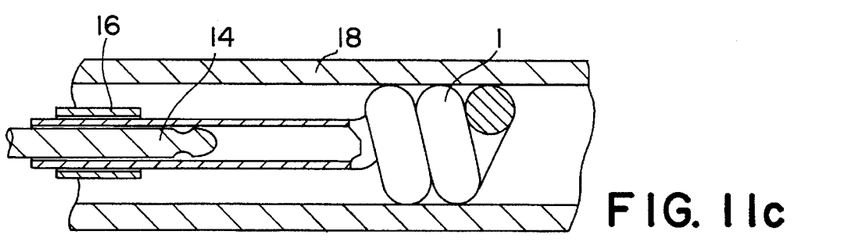
Figure 11D:
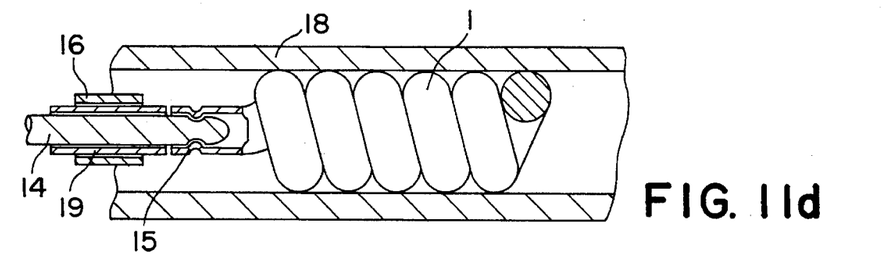
Figure 11E:
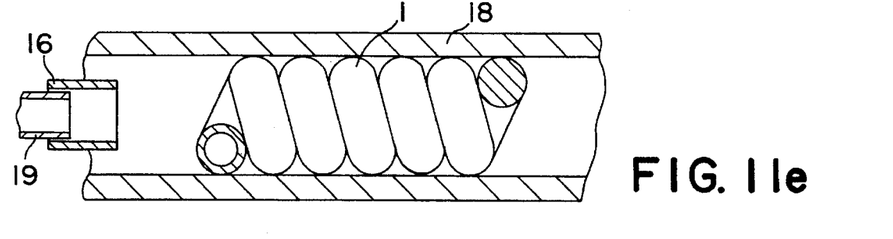

FIGS. 10a–c show the preferably strengthened catheter tip in cross-section.

FIG. 10a shows a round catheter 16 with an inserted cylindrical liner 17.

In FIG. 10b, an oval catheter 16 is represented with a rectangular liner 17, and in FIG. 10c an oval catheter 16 with a rectangular liner 17 into which an implant 1 has been retracted.

This rectangular shape of a liner 17 is particularly preferred when the primary shape of the implant 1 possesses an oval rather than a round cross-section.

FIGS. 11a–e show diagrammatically the positioning of the implant 1 in an organ pathway 18, for example a blood vessel. A catheter 16 is pushed inside the organ pathway 18 into the vicinity of the site at which the implant 1 is to be positioned. The implant 1 is located, in an extended condition in the so-called primary shape, in the inner lumen of the catheter and on the insertion wire 14. Starting from the distal end of the catheter, which end is located outside the body, the guide wire 14, with the implant 1 located on it in extended form, is pushed forward into the organ pathway 18 to the site for positioning. In step B, the secondary shape of the implant is formed, from the primary shape of the implant 1 and as a result of the spring action, in the organ pathway 18 by withdrawing the guide wire 14 or by pushing forward the stripping element 19. In step C, the secondary shape of the implant 1 is developed further by withdrawing the insertion catheter 16 and by further withdrawal of the guide wire 14, or by pushing forward the stripping element 19, and in step D the position is reached in which the guide wire 14 is contained in the last section of the primary shape of the implant 1 and the clamping seat, due to the modified cross-section 7 of the primary shape of the implant 1, is still present on the guide wire 14. In the embodiment of the guide wire represented in step D, the wire possesses an annular groove 15 in which the wall of the modified cross-section of the primary shape, for example one or more spirals of a wire 6 having a smaller cross-section, or at least a cross-section which is reduced in one direction, engages. In this position there is, after checking for the correct positioning of the implant 1 in the organ pathway 18, a final chance to withdraw the unrolled secondary shape of the implant 1 into the catheter 16 by pulling back the guide wire. The fact that the force required to overcome the clamping seat amounts to several times that required to reextend the formed secondary shape of the implant 1 and draw it back into the catheter 16 ensures that it is possible to reposition the implants according to the invention in the case of an incorrect arrangement or an unsuitable choice of shape. A stripping element 19 is arranged on the guide wire 14 in an axial direction behind the primary shape of the implant 1, the posterior end of which element reaches to the distal end of the catheter. The stripping element can be a tube or else, for reasons of elasticity, a spiral, whose external diameter coincides with the external diameter of the primary shape of the implant at its posterior end. By pushing forward the stripping element 19 in the catheter 16 or pulling back the guide wire 14 while keeping the stripping element 19 stationary, the clamping seat of the implant 1 on the guide wire 14 is released, and the end of the guide wire is pulled out of the shape, or the primary shape is stripped off from the end of the guide wire. The implant 1 then assumes the predetermined shape in the organ pathway 18. Catheter 16 and stripping element 19 are withdrawn from the organ pathway.

In the case of a tandem arrangement of implants, two primary shapes, preferably implants having the double-cone shape, are extended in a tandem arrangement on a guide wire. The first implant is initially positioned in the organ pathway, and then the second implant is unrolled and positioned in the inner lumen of this implant. In the case of double-coned implants, it is possible to arrange them so that at least a part of the central section of the second implant remains in extended form and thus exerts a traction effect on the ends of the double-coned first implant.

The particular advantage of the configuration of spiral implants according to the invention is that the implant can still be manipulated even in the implanted state as long as it has still not been completely uncoupled from the guide wire. The repositionability which this provides represents the crucial improvement as compared with conventional technology. Following thrombosis in the region of the implant, a lasting. occlusion of the organ pathway, for example of blood vessels, is provided. If resorbable implant materials having a spring action are used, no undesirable side-effects are to be expected, even over a long period of time. The exact positioning can be monitored radiologically or by means of ultrasonics.

I claim:

1. An implant for insertion into a vessel of an organ comprising an elongated tubular conduit having anterior and posterior ends, said conduit defining a lumen having an inner surface and an outer surface defining internal and external diameters, respectively, said conduit being made from a material having restitutory forces; and said interior end being closed and a posterior region at the posterior end having means forming a clamping seat sized to engage a guide wire having an anterior end; and said implant having a distended first configuration when said guide wire is inserted within the tubular conduit and a second configuration when said guide wire is removed from the tubular conduit, said second configuration being effected by the restitutory forces of the material, wherein said means forming the clamping seat is a radial constriction of the internal diameter beginning about 0.5 mm to 2 mm from said posterior end and extending to a length of about 0.1 mm to 10 mm.

2. An implant as defined in claim 1, wherein the conduit consists of a primary spiral made of metal.

3. An implant as defined in claim 2, wherein the primary spiral has a diameter and is made of wire having a wire diameter of from 0.06 to 0.6 mm, and wherein the diameter of the primary spiral is from 0.2 to 3 mm.

4. An implant as defined in claim 2, wherein the cross-section of at least one to several turns of the primary spiral is modified by constricting the diameter of the primary spiral.

5. An implant as defined in claim 2, wherein the primary spiral is wound from a wire having a cross-section chosen from the group consisting of round, oval and rectangular.

6. An implant as defined in claim 2, wherein the force required to displace the conduit and to overcome the clamping force exercised by the clamping seat on the guide wire is 0.5N to 10N.

7. An implant as defined in claim 6, wherein the guide wire is provided, at its anterior end or in the vicinity of this end, either with an annular groove or with a circumferential beading.

8. An implant as defined in claim 2, wherein the cross-section of at least one to several turns of the primary spiral is modified by flattening the primary spiral so that it assumes an oval cross-section.

9. An implant as defined in claim 1, wherein the conduit consists of a primary tube, having a diameter, made of elastic synthetic material.

10. An implant as defined in claim 9, wherein the primary tube has a wall with a thickness of from 0.08 mm to 0.8 mm and the diameter of the primary tube is from 0.3 to 3 mm.

11. An implant as defined in claim 9, wherein the cross-section of the primary tube is modified by constricting the diameter of a portion of the primary tube.

12. An implant as defined in to claim 9, wherein the cross-section of the primary tube is modified by forming a portion of the primary tube with an oval cross-section having a reduced diameter in one direction as compared with the diameter of the remainder of the primary tube.

13. An implant as defined in claim 1, wherein the conduit is 10 to 500 mm long.

14. An implant as defined in claim 1, wherein the second configuration of the conduit has a form chosen from the group consisting of a cylinder, a cone, a double cone with larger diameters at the ends, a cylinder in which turns of the second configuration having different diameters alternate, a double helix which is connected by a cylindrical section, a double rosette, and the form of several horizontal figures of eight.

15. An implant as defined in claim 14, wherein the double cone, double helix and double rosette have inner and outer turns, said inner turns being composed of a primary spiral having a round wire cross-section, and said outer turns being composed of a primary spiral having an enlarged wire cross-section chosen from the group consisting of round, oval and rectangular.

16. A process for positioning the implant defined in claim 1 in an organ pathway by means of the steps:

a) advancement of an insertion catheter, in whose inner lumen the implant is located in the distended first configuration on the guide wire, inside the organ pathway into the vicinity of the site where the implant is to be located, b) displacement of the guide wire, with the implant located on it in the distended first configuration, to the intended site for the implant's location, c) formation of the second configuration of the implant by withdrawing the guide wire or by pushing forward a stripping element, d) further withdrawal of the catheter and of the guide wire, or pushing forward of the stripping element, until only the anterior end of the guide wire is held in the clamping seat in the posterior region of the conduit, e) correction of the position of the implant, or, withdrawal of the implant into the catheter, f) stripping-off of the implant from the guide wire at the site intended for it in the organ pathway using the stripping element.

* * * * *

UNITED STATES PATENT AND TRADEMARK OFFICE
CERTIFICATE OF CORRECTION

PATENT NO.:   5,536,274

DATED:        July 16, 1996

INVENTOR(S):  Malte NEUSS

It is certified that error appears in the above-identified patent and that said Letters Patent is hereby corrected as shown below:

On the title page, item [86], the § 371 date should be "Oct. 1, 1993".

On the cover page, item [73], "pfm Produkterfür Die Medizin" should read --pfm Produkte für die Medizin GmbH--.

Signed and Sealed this

Third Day of December, 1996

*Attest:*

BRUCE LEHMAN

*Attesting Officer*   Commissioner of Patents and Trademarks